United States Patent
Ware et al.

(10) Patent No.: US 7,811,819 B2
(45) Date of Patent: Oct. 12, 2010

(54) CRYOPRESERVATION OF PRIMATE EMBRYONIC STEM CELLS

(75) Inventors: Carol Ware, Bainbridge Isl., WA (US); Angelique M. Nelson, Seattle, WA (US)

(73) Assignee: The University of Washington, Seattle, WA (US)

( * ) Notice: Subject to any disclaimer, the term of this patent is extended or adjusted under 35 U.S.C. 154(b) by 739 days.

(21) Appl. No.: 11/142,651

(22) Filed: May 31, 2005

(65) Prior Publication Data

US 2006/0269908 A1 Nov. 30, 2006

(51) Int. Cl.
C12N 5/00 (2006.01)
C12N 5/02 (2006.01)
C12N 5/06 (2006.01)
C12N 5/08 (2006.01)

(52) U.S. Cl. .................. 435/374; 435/325; 435/363; 435/366

(58) Field of Classification Search ............. 435/325, 435/363, 366, 374
See application file for complete search history.

(56) References Cited

OTHER PUBLICATIONS

Heng et al., Apr. 2005, Biotechnology and Applied Biochemistry, vol. 41, Part 2, pp. 97-104.*
Ware et al., Jun. 2005, BioTechniques, vol. 38, No. 6, pp. 879-880, 882-883.*
Richards, et al., 2004, Stem Cells, vol. 22, p. 779-789.*
Ha et al., 2005, Human Reproduction, vol. 20, No. 7, pp. 1779-1785.*
Fujioka et al., A Simple and Efficient Cryopreservation Method for Primate Embryonic Stem Cells, 2004, Int. J. Dev. Biol., 48: 1149-1154.
Heng et al., The Cryopreservation of Human Embryonic Stem Cells, 2004, Biotechnol. Appl. Biochem., 1-21 (manuscript).
Ji et al., Cryopreservation of Adherent Human Embryonic Stem Cells, 2004, Biotechnol. Bioeng. 88(3): 299-312.
Kim et al., Effects of Type IV Collagen and Laminin on the Cryopreservation of Human Embryonic Stem Cells, 2004, Stem Cells, 22:950-961.
Leibo et al., 1978, (Methods in Mammalian Reproduction) Methods for the Preservation of Mammalian Embryos by Freezing, Chap. 8, 179-201.
Leibo et al., 1981, (New Technologies in Animal Breeding) Preservation of Ova and Embryos by Freezing, Academic Press, Inc., 1981, 127-139.
Mazur et al., (The Freezing of Mammalian Embryos) Slow Freezing Injury in Mammalian Cells, 1977, 19-48.
Reubinoff et al., 2001, Effective Cryopreservation of Human Embryonic Stem Cells by the Open Pulled Straw Vitrification Method, Human Reprod., 16(10): 2187-2194.

* cited by examiner

*Primary Examiner*—Shin-Lin Chen
(74) *Attorney, Agent, or Firm*—Bozicevic, Field & Francis LLP; Pamela J. Sherwood

(57) ABSTRACT

Primate embryonic stem cells are cryopreserved by resuspension in a freezing medium and slow cooling at a controlled rate. In some embodiments, prior to the controlled freezing step, the suspension of cells is cooled to a temperature just below freezing, and ice crystal formation is induced. The cryopreserved cell aggregates are useful in transplantation, for experimental evaluation, and as a source of lineage and cell specific products, and as targets for the discovery of factors or molecules that can affect them.

11 Claims, 3 Drawing Sheets

CRYOPRESERVATION OF PRIMATE EMBRYONIC STEM CELLS

BACKGROUND OF THE INVENTION

The growth potential of mammalian embryonic stage cells have been known for many years, but the ability to culture such pluripotent and totipotent stem cells, particularly human stem cells, has only been recently developed. Stem cells have a capacity both for self-renewal and the generation of differentiated cell types. Embryonic stem (ES) cells are derived from cultures of inner cell mass (ICM) cells, and have the property of participating as totipotent cells when placed into host blastocysts. The developmental pathways that endogenous ICM cells or transferred ES cells take to tissue formation and organogenesis has led many to hope that these pathways can be controlled for the development of tissue and organ specific stem cells.

Human ES cells have a variety of research and potential clinical uses. Diseases that might be treated by transplanting human ES-derived cells include Parkinson's disease, diabetes, traumatic spinal cord injury, Purkinje cell degeneration, Duchenne's muscular dystrophy, heart failure, and osteogenesis imperfecta. One of the advantages of using ES cells as compared to adult stem cells is that ES cells have an unlimited ability to proliferate in vitro, and are more likely to be able to generate a broad range of cell types through directed differentiation.

Human ES cells can also be used to study early events in human development. Still-unexplained events in early human development can result in congenital birth defects and placental abnormalities that lead to spontaneous abortion. By studying human ES cells in vitro, it may be possible to identify the genetic, molecular, and cellular events that lead to these problems and identify methods for preventing them. Such cells could also be used to explore the effects of chromosomal abnormalities in early development. This might include the ability to monitor the development of early childhood tumors, many of which are embryonic in origin.

Human ES cells can also be used to test candidate therapeutic drugs. Currently, before candidate drugs are tested in human volunteers, they are subjected to a barrage of preclinical tests. These include drug screening in animal models—in vitro tests using cells derived from mice or rats, for example, or in vivo tests that involve giving the drug to an animal to assess its safety. Although animal model testing is a mainstay of pharmaceutical research, it cannot always predict the effects that a candidate drug may have on human cells. For this reason, cultures of human cells are often employed in preclinical tests. These human cell lines have usually been maintained in vitro for long periods and as such often have different characteristics than do in vivo cells. These differences can make it difficult to predict the action of a drug in vivo based on the response of human cell lines in vitro.

Human ES cells can also be employed to screen potential toxins. The reasons for using human ES cells to screen potential toxins closely resemble those for using human ES-derived cells to test drugs (above). Toxins often have different effects on different animal species, which makes it critical to have the best possible in vitro models for evaluating their effects on human cells.

Human and mouse ES cells differ in morphology, immunophenotype, and growth properties. While mouse ES cells grow in attached rounded masses in which single cells are difficult to identify, the primate cells grow in flat colonies with varying distinctness of cell borders in monolayer culture. Like mouse ES and embryonic germ (EG) cells, primate pluripotent cells, including some human EC cells, require a mouse embryonic fibroblast feeder-cell layer for support. In the case of mouse ES and EG cells, the feeder cell requirement can be replaced by LIF or related members of this cytokine family, but pluripotent human EC cells, rhesus monkey ES cells, and human ES cells will not respond to LIF in such a fashion. Even on a feeder cell layer, all primate pluripotent cells grow very poorly when dissociated to single cells, whereas mouse ES cell lines can be cloned at a relatively high efficiency in the presence of LIF under these conditions.

For many purposes, it is desirable to have the ability to store human or other primate ES cells for long periods of time. Mouse ES cells are conveniently frozen, or cryopreserved, for such purposes. However, such methods have not proven to provide for viable cryopreservation of primate ES cells.

There are previously reported techniques for hESC cryopreservation. Reubinoff et al., 2001, Human Reprod. 16, 2187 describes a vitrification method, and Ji et al., 2004, Biotechnol. Bioeng. 88, 299 describes freezing cells in adherent culture within a matrigel matrix. The vitrification technique is technically challenging. High levels of cryoprotectants are toxic at room temperature requiring strict attention to time and temperature constraints during freeze and thaw, cell growth following thaw is not robust and the freezing container has such a large surface to volume ratio that the cells are sensitive to routine handling while frozen. The matrix embedding method improves survival over standard freezing. However, because hESC are frozen adherent to the culture dish, liquid nitrogen storage becomes problematic since most liquid nitrogen storage vessels are not designed to hold culture plates. They can be conveniently stored at −80° C. But, −80° C. storage substantially reduces the time cells can maintain viability while frozen. In addition, freezing in a matrix must be anticipated by at least 24 hours.

Methods that provide for stable storage and high viability of primate ES cells are of great interest for many purposes. The present invention addresses these needs.

Publications

Mazur (1977), "Slow freezing injury in mammalian cells", p. 19-42. In K. Elliott and J. Whelan (Eds.), The Freezing of Mammalian Embryos, Ciba Found. Symp. 52, Elsevier Excerpta Medica, Amsterdam. Leibo and Mazur (1978) "Methods of the preservation of mammalian embryos by freezing", p. 179-201. In J. C. Daniel Jr., (Ed.) Methods of Mammalian Reproduction, Academic Press, New York, N.Y. Leibo (1981) "Preservation of ova and embryos by freezing", p. 127-139. In B. G. Brackett, G. E. Seidel Jr., S. M. Seidel (Eds.) New Technologies in Animal Breeding. Academic Press, New York, N.Y. Heng et al. (2004) The Cryopreservation of Human Embryonic Stem Cells" Biotechnol. & Appl. Biochem. Kim et al. (2004) Stem Cells 22:950-961, "Effects of Type IV Collagen and Laminin on the Cryopreservation of Human Embryonic Stem Cells." Fujioka et al. (2004) Int. J. Dev. Biol. 48:1149-1154, "A Simple and Efficient Cryopreservation Method for Primate Embryonic Stem Cells."

SUMMARY OF THE INVENTION

Methods are provided for the cryoporeservation of primate embryonic stem cells. An in vitro culture of primate ES cells is partially dissociated, to generate a population of cell aggregates. The aggregates are resuspended in a freezing medium. In some embodiments, prior to the controlled freezing step, the suspension of cells is cooled to a temperature just below freezing, and ice crystal formation is induced. At this point they are slow cooled at a controlled rate. The cells can be stored at from about −80° C., to about −196°, for example in liquid nitrogen. Thawing is accomplished by rapidly bringing the cells up to temperature. The cells retain a high viability upon thawing.

The cryopreserved cell aggregates are useful in transplantation, for experimental evaluation, and as a source of lineage and cell specific products, and as targets for the discovery of factors or molecules that can affect them.

These and other embodiments of the invention will be apparent from the description that follows. The compositions, methods, and techniques described in this disclosure hold considerable promise for use in diagnostic, drug screening, and therapeutic applications.

DETAILED DESCRIPTION OF THE EMBODIMENTS

Figure 1:
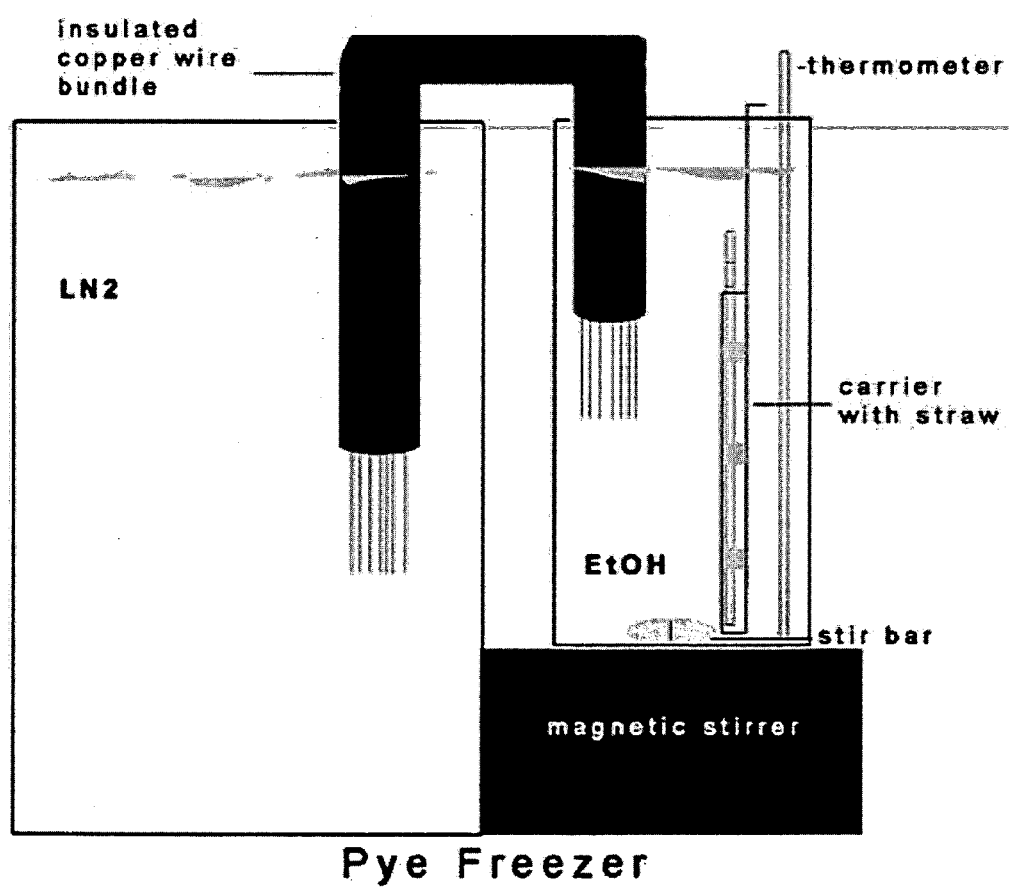
FIG. 1. Representation of the Pye Freezer. Bundles of insulated copper wires are draped between a liquid nitrogen and an ethanol bath. The ethanol bath holds the straw containing the hESC and is mixed using a magnetic stirrer to achieve a homogenous temperature.

Primate ES cell lines are frozen at a controlled, slow rate, to provide for cryopreserved samples. Following rapid thawing, the samples have high viability, and are suitable for research or therapeutic purposes. In the methods of the invention, cell aggregates from an in vitro culture of primate ES cells are resuspended in a freezing medium. In some embodiments, the suspension is then cooled to a temperature just below freezing, and ice crystal formation is induced. The suspension is then slow cooled at a controlled rate. The methods provide a means for storing primate, particularly human, ES cells for extended periods of time without significant loss of viability.

Compositions

Pluripotent stem cells are cells derived from any kind of tissue (usually embryonic tissue such as fetal or pre-fetal tissue), which stem cells have the characteristic of being capable under appropriate conditions of producing progeny of different cell types that are derivatives of all of the 3 germinal layers (endoderm, mesoderm, and ectoderm). These cell types may be provided in the form of an established cell line, (for example as set forth in U.S. Pat. Nos. 5,843,780 and 6,200,806, herein incorporated by reference), or they may be obtained directly from primary embryonic tissue. Included are cells listed in the NIH Human Embryonic Stem Cell Registry, e.g. hESBGN-01, hESBGN-02, hESBGN-03, hES-BGN-04 (BresaGen, Inc.); HES-1, HES-2, HES-3, HES-4, HES-5, HES-6 (ES Cell International); Miz-hES1 (MizMedi Hospital-Seoul National University); HSF-1, HSF-6 (University of California at San Francisco); and H1, H7, H9, H13, H14 (Wisconsin Alumni Research Foundation (WiCell Research Institute)).

Stem cells of interest also include embryonic cells of various species, exemplified by human embryonic stem (hES) cells, described by Thomson et al. (1998) Science 282:1145; embryonic stem cells from other primates, such as Rhesus stem cells (Thomson et al. (1995) Proc. Natl. Acad. Sci USA 92:7844); marmoset stem cells (Thomson et al. (1996) Biol. Reprod. 55:254); and human embryonic germ (hEG) cells (Shamblott et al., Proc. Natl. Acad. Sci. USA 95:13726, 1998).

The cryopreserved ES cells maintain an undifferentiated state during the cryopreservation and thawing process. Cells are considered to be undifferentiated when they have not committed to a specific differentiation lineage. Undifferentiated ES cells are easily recognized by those skilled in the art, and typically appear in the two dimensions of a microscopic view in colonies in which the cells have a high nuclear/cytoplasmic ratio and prominent nucleoli. Undifferentiated ES cells express genes that may be used as markers to detect the presence of undifferentiated cells, and whose polypeptide products may be used as markers for negative selection. For example, see US 2003/0224411 A1; Bhattacharya (2004) Blood 103(8):2956-64; and Thomson (1998), supra., each herein incorporated by reference. Human ES cell lines express cell surface markers that characterize undifferentiated nonhuman primate ES and human EC cells, including stage-specific embryonic antigen (SSEA)-3, SSEA-4, TRA-I-60, TRA-1-81, and alkaline phosphatase. The globo-series glycolipid GL7, which carries the SSEA-4 epitope, is formed by the addition of sialic acid to the globo-series glycolipid Gb5, which carries the SSEA-3 epitope. Thus, GL7 reacts with antibodies to both SSEA-3 and SSEA-4. The undifferentiated human ES cell lines did not stain for SSEA-1, but differentiated cells stained strongly for SSEA-I. Methods for proliferating hES cells in the undifferentiated form are described in WO 99/20741, WO 01/51616, and WO 03/020920.

Cryopreserved ES cells. Compositions of cryopreserved ES cells comprise frozen aggregates of primate ES cells and a freezing medium, which may be provided in any suitable container, particularly vials or straws.

The degree of aggregation as referred to herein will be understood to be a mean value, where a normal distribution of sizes will be observed in a population. Aggregates will usually comprise at least about 25 cells, usually at least about 50 cells, and not more than about 200 cells, usually not more than about 150 cells, more usually not more than about 100 cells. The average size of an aggregate is usually around about 80 μM, 100 μM or 120 μM. The size of aggregate is an important factor in viability, where both larger and smaller values lead to decreased viability.

As used herein, cryopreserved ES cells are stored frozen at a temperature of at least about −80° C., but preferably at a much colder temperature, e.g. at least about −145° C., at least about −150° C., or less, typically down to the temperature of liquid nitrogen, at approximately −195° C. At these temperatures, particularly in liquid nitrogen, the cells may be maintained for extended periods of time, e.g. for about one year, ten years, 20 years, or longer, while maintaining viability.

The viability of the cryopreserved cells is determined after the cells are thawed, where the thawing is performed according to the methods of the invention. The viability of the cells is usually at least about 50%, more usually at least about 70%, and may be 80% or greater.

Methods of Cryopreservation

ES cells or cell lines can be propagated continuously in culture, using culture conditions that promote proliferation without promoting differentiation, using methods known in the art. Methods of culture are described, for example, in U.S. Patent application 20030190748 (Serum free cultivation of primate embryonic stem cells); U.S. Patent application 20040023376 (Method of making embryoid bodies from primate embryonic stem cells); U.S. Patent application 20030008392 (Primate embryonic stem cells), each herein incorporated by reference. Conventionally, ES cells are cultured on a layer of feeder cells, typically fibroblasts derived from embryonic or fetal tissue, alternatively cells can be cultured on an extracellular matrix of Matrigel™ or laminin, in medium conditioned by feeder cells or medium supplemented with growth factors such as FGF and SCF (International patent publication WO 01/51616). Under the microscope, ES cells appear with a high nuclear/cytoplasmic ratio, prominent nucleoli, and compact colony formation with poorly discernable cell junctions.

The culture of cells is partially digested, so as to minimize the disruption to the cells. The digestion usually involves exposing the cells to a mild protease, e.g. dispase, collagenase, blendzyme, elastase, etc., and/or chelators, as known in the art using time, temperature, concentration and selection of reagents that will achieve a partial digestion that leaves aggregates of cells. One of skill in the art can readily perform a simple titration to determine suitable conditions. In certain embodiments, the cells are not mechanically disrupted in the absence of an enzymatic treatments to remove the cells from the growth substrate, i.e. plate, flask, etc.

The cell aggregates are resuspended in a suitable freezing medium, preferably a medium that is not toxic to the cells at room temperature. Suitable medium comprises a physiologically acceptable buffer, e.g. PBS, DMEM, Iscove's etc., glucose at a concentration of from about 1000 to about 5000 mg/L, usually about 4500 mg/L; from at least about about 5% to not more than about 15%, usually at least about 10% of a cryoprotectant, such as DMSO, glycerol, etc. The freezing medium may further comprise at least about 10%, more usually at least about 20%, and not more than about 90%, usually not more than about 25% serum or serum substitute, e.g. fetal bovine serum, albumin, serum replacement, etc. In some embodiments of the invention, the freezing medium is free of added proteins such as Type IV collagen and/or laminin.

The suspension of cells is aliquoted into a suitable closed container, e.g. small vials, closed straws, etc., usually other than a large container or open container. In a preferred embodiment, the suspension of cells is cooled to a temperature just below 0° C., e.g. at about −1° C., usually not more than about −5° C., to not less than about −12° C., for a period of time sufficient to supercool the suspension, usually from about 1 minute to not more than 10 minutes, more usually from about 2 minutes to not more than about 5 minutes. Ice crystal formation is induced by contacting the outer surface of the container with a probe chilled to less than than about −100° C., e.g. dipped in liquid nitrogen. Probes for such a purpose include, without limitation, forceps, rings, etc.

The suspension of cells is then slowly cooled under controlled conditions, where the temperature drop is at least about −0.3°/minute and not more than about −2° C. per minute, and may comprise any value between, e.g. −0.5°/minute, −1°/minute, −1.5°/minute, −1.8°/minute, etc. Suitable mechanisms for such controlled rate freezing are known in the art, and include commercial freezers specifically designed for such a purpose; or an assembled device, the Pye freezer, for example as shown in FIG. 1; and the like. The suspension of cells is slow cooled to a temperature of not more than about −30° C., usually not more than about −33° C., and may be cooled to lower temperatures if desired. The sample is then rapidly cooled to the final freezing temperature, e.g. by immersing in liquid nitrogen.

As described above, the cryopreserved sample may be maintained at low temperatures for extended periods of time. For culture or therapeutic purposes, the cells are thawed rapidly, conveniently by contacting with a bath at from about 15° C. to about 37° C., usually at a bath at from about 20° C. to about 37° C.

The compositions thus obtained have a variety of uses in clinical therapy, research, development, and commercial purposes. For therapeutic purposes, for example, ES cells or their progeny may be administered to enhance tissue maintenance or repair for any perceived need, such as an inborn error in metabolic function, the effect of a disease condition, or the result of significant trauma.

To determine the suitability of cell compositions for therapeutic administration, the cells can first be tested in a suitable animal model. At one level, cells are assessed for their ability to survive and maintain their phenotype in vivo. Cell compositions are administered to immunodeficient animals (such as nude mice, or animals rendered immunodeficient chemically or by irradiation). Tissues are harvested after a period of regrowth, and assessed as to whether the administered cells or progeny thereof are still present.

This can be performed by administering cells that express a detectable label (such as green fluorescent protein, or β-galactosidase); that have been prelabeled (for example, with BrdU or [$^3$H]thymidine), or by subsequent detection of a constitutive cell marker (for example, using human-specific antibody). The presence and phenotype of the administered cells can be assessed by immunohistochemistry or ELISA using human-specific antibody, or by RT-PCR analysis using primers and hybridization conditions that cause amplification to be specific for human polynucleotides, according to published sequence data.

The cells may be administered in any physiologically acceptable excipient, where the cells may find an appropriate site for regeneration and differentiation. The cells may be introduced by injection, catheter, or the like. Once thawed, the cells may be expanded by use of growth factors and/or feeder cells associated with progenitor cell proliferation and differentiation.

The cells of this invention can be supplied in the form of a pharmaceutical composition, comprising a freezing medium prepared under sufficiently sterile conditions for human administration. For general principles in medicinal formulation, the reader is referred to Cell Therapy: Stem Cell Transplantation, Gene Therapy, and Cellular Immunotherapy, by G. Morstyn & W. Sheridan eds, Cambridge University Press, 1996; and Hematopoietic Stem Cell Therapy, E. D. Ball, J. Lister & P. Law, Churchill Livingstone, 2000. Choice of the cellular excipient and any accompanying elements of the composition will be adapted in accordance with the route and device used for administration. The composition may also comprise or be accompanied with one or more other ingredients that facilitate the engraftment or functional mobilization of the cells.

For further elaboration of general techniques useful in the practice of this invention, the practitioner can refer to standard textbooks and reviews in cell biology, tissue culture, embryology, and cardiophysiology. With respect to tissue culture and embryonic stem cells, the reader may wish to refer to Teratocarcinomas and embryonic stem cells: A practical approach (E. J. Robertson, ed., IRL Press Ltd. 1987); Guide to Techniques in Mouse Development (P. M. Wasserman et al. eds., Academic Press 1993); Embryonic Stem Cell Differentiation in Vitro (M. V. Wiles, Meth. Enzymol. 225:900, 1993); Properties and uses of Embryonic Stem Cells: Prospects for Application to Human Biology and Gene Therapy (P. D. Rathjen et al., Reprod. Fertil. Dev. 10:31, 1998). With respect to the culture of heart cells, standard references include The Heart Cell in Culture (A. Pinson ed., CRC Press 1987), Isolated Adult Cardiomyocytes (Vols. I & II, Piper & Isenberg eds, CRC Press 1989), Heart Development (Harvey & Rosenthal, Academic Press 1998), General methods in molecular and cellular biochemistry can be found in such standard textbooks as Molecular Cloning: A Laboratory Manual, 3rd Ed. (Sambrook et al., Harbor Laboratory Press 2001); Short Protocols in Molecular Biology, 4th Ed. (Ausubel et al. eds., John Wiley & Sons 1999); Protein Methods (Bollag et al., John Wiley & Sons 1996); Nonviral Vectors for Gene Therapy (Wagner et al. eds., Academic Press 1999); Viral Vectors (Kaplift & Loewy eds., Academic Press 1995); Immunology Methods Manual (I. Lefkovits ed., Academic Press 1997); and Cell and Tissue Culture: Laboratory Procedures in Biotechnology (Doyle & Griffiths, John Wiley & Sons 1998). Reagents, cloning vectors, and kits for genetic manipulation referred to in this disclosure are available from commercial vendors such as BioRad, Stratagene, Invitrogen, Sigma-Aldrich, and ClonTech.

The following examples are put forth so as to provide those of ordinary skill in the art with a complete disclosure and description of how to make and use the present invention, and are not intended to limit the scope of what the inventors regard as their invention nor are they intended to represent that the experiments below are all or the only experiments performed. Efforts have been made to ensure accuracy with respect to numbers used (e.g. amounts, temperature, etc.) but some experimental errors and deviations should be accounted for. Unless indicated otherwise, parts are parts by weight, molecular weight is weight average molecular weight, temperature is in degrees Centigrade, and pressure is at or near atmospheric.

All publications and patent applications cited in this specification are herein incorporated by reference as if each individual publication or patent application were specifically and individually indicated to be incorporated by reference.

The present invention has been described in terms of particular embodiments found or proposed by the present inventor to comprise preferred modes for the practice of the invention. It will be appreciated by those of skill in the art that, in light of the present disclosure, numerous modifications and changes can be made in the particular embodiments exemplified without departing from the intended scope of the invention. For example, due to codon redundancy, changes can be made in the underlying DNA sequence without affecting the protein sequence. Moreover, due to biological functional equivalency considerations, changes can be made in protein structure without affecting the biological action in kind or amount. All such modifications are intended to be included within the scope of the appended claims.

EXPERIMENTAL

Example 1

Controlled-Rate Freezing of Human ES Cells

A significant obstacle to using human embryonic stem cells (hESC) arises from extremely poor survival associated with freezing, typically in the range of 1%. The data provided herein provides a method where a slow, controlled-rate freezing technique is used. Using a combination of surviving colony number and colony diameter, survival was determined relative to untreated hESC. Using a DMSO cryoprotectant, an ~80% survival following slow, controlled-rate cooling was achieved. The critical factors were an ice crystal seed (at −7 to −10° C.), a freeze rate between 0.3 and 1.8° C. per minute and a rapid thaw rate using room temperature water. An inexpensive controlled-rate freezing device was compared to a commercial machine and was shown to allow equivalent survival. Slow, controlled-rate cooling allows a rapid, simple and reproducible means of cryopreserving hESC.

We have tested various parameters that are known to be important for successful cryopreservation to develop a technique that is widely applicable to human embryonic stem cells (hESC). This is both timely and important in that most hESC are currently frozen by techniques that lead to extremely poor recovery following thaw, typically less than 1%. This has impacted the use of hESC. hESC lines are commonly sent conventionally frozen. Laboratories that have not previously handled the cells experience time consuming recovery frequently ending in failure. In laboratories that are familiar with hESC culture, poor recovery following freezing significantly prolongs the time it takes to grow enough cells to complete experiments and has the effect of keeping cells in culture to higher passage numbers rather than using low passage number, well characterized hESC for critical experiments.

Because hESC are passaged in clumps and are not routinely digested into single cell suspension, freezing requirements might approximate those of mammalian embryos. Techniques developed for mammalian embryo freeze-storage have identified two basic methods, slow controlled-rate cooling and rapid cooling through vitrification. An open pulled straw vitrification procedure was recently described that yielded an increase in hESC survival. Improved survival was accompanied by a tendency toward retarded growth and increased differentiation, which resolved upon culture for 9 days following thaw. Vitrification, though inexpensive and effective, requires cryoprotectant levels that are toxic to cells at room temperature, necessitating adherence to strict time and temperature constraints and is the likely reason for the temporary alteration in growth noted following thaw. In addition, straws need to be pulled to maximize surface to volume ratio, which can leave the cells more vulnerable to subtle temperature changes experienced through handling during liquid nitrogen ($LN_2$) storage. Consequently, vitrification success can be erratic, particularly during the learning process.

Slow, controlled-rate freezing is technically less challenging although it requires the use of a controlled-rate freezing unit. To reduce cost and improve availability of the process, we compare survival of the cells using a simple, inexpensive, easily made freezing device (Pye freezer) to a commercially available controlled-rate freezing unit. We describe a technique that allows 79% (±15%) hESC survival on thaw with no apparent increase in differentiation.

Materials and Methods hESC culture. H1 hESC from passage 51 to 57 (WiCell, Madison, Wis., USA) were cultured in Knockout™ DMEM supplemented with GlutaMAX™ (2 mM), sodium pyruvate (1.0 mM), non-essential amino acids (0.1 mM), penicillin (50 u/ml), streptomycin (50 u/ml), Knockout™ serum replacer (15%) (all from Invitrogen, Carlsbad, Calif., USA) and β-mercaptoethanol (0.1 mM; Sigma, St. Louis, Mo., USA). hESC were grown on gelatinized tissue culture plates seeded with primary mouse embryonic fibroblasts that had been exposed to 3000 Rads γ-irradiation. To passage, cells were washed once with calcium and magnesium free phosphate buffered saline (PBS; Invitrogen, Carlsbad, Calif., USA) and then exposed to 1.2 u/ml dispase (Invitrogen, Carlsbad, Calif., USA) dissolved in PBS supplemented with 10% FBS until colonies began to lift from the plate. The cell layer was washed off the plate and mechanically dispersed using a plugged 9-inch Pasteur pipette or a 5 ml pipette. At this point, cells were divided into tubes for each group. The cells were then pelleted through centrifugation at 1200 rpm for 3 minutes, washed and pelleted again in culture medium (described above). Control cells (Group 1) were resuspended in culture medium for immediate replating onto one well of a 6-well plate seeded with primary mouse fibroblast feeder layers. The average cluster diameter following disaggregation was 106 µM (±5.8).

All other cells were treated as described below.

Cryopreservation. Cells were suspended in freezing medium [high glucose DMEM (Invitrogen, Carlsbad, Calif., USA) containing penicillin (50 u/ml), streptomycin (50 µg/ml), 25% fetal bovine serum (ES cell qualified, Invitrogen, Carlsbad, Calif.) and 10% DMSO (Sigma, St. Louis, Mo., USA)]. Cells were drawn into 0.25 ml Cassou straws (Edwards Agri-Sales, Menomonie, Wis., USA) using a 1 ml syringe affixed to the plug end of the straw. Straws were held at room temperature for 20 minutes. Straws destined to explore the toxicity of the DMSO cryoprotectant (Group 2) were emptied without freezing into a tube containing culture medium and plated as described below. Rapid freeze (Group 3) straws were placed directly at −80° C., then plunged into $LN_2$ 20 minutes later. Straws destined for controlled-rate cooling were placed directly at −7° C. (Group 9) or −10° C. (Groups 5-8, 10 & 11) and held for 2-5 minutes. Those that were not to be seeded (Group 4) were left undisturbed and straws destined for ice crystal seeding (Groups 5-11) were touched with $LN_2$ cooled forceps on the outside of the straw to induce an ice crystal to form inside the straw. Freezing of the medium in the straw was allowed to proceed for 5 minutes before controlled-rate cooling was begun. Groups 4-8 were frozen at 1° C./minute, Group 10 at 1.8° C./minute and Group 11 at 2.7° C. per minute. Groups 8 and 11 were frozen in the Pye freezer and Groups 4-7, 9 and 10 were frozen in a Bio-Cool III Programmable Freezer (FTS Kinetics, Stone Ridge, N.Y., USA). Upon reaching −33° C., all frozen straws were plunged into liquid nitrogen and held for at least 5 minutes at −196° C. before thaw. Group 9 was frozen at 0.3° C. per minute to −33° C. followed by a drop of 0.1° C. per minute down to −35° C., when straws were plunged into $LN_2$. Upon thaw, all straws were rinsed with ethanol, dried, and the contents directly emptied into tubes containing 5 ml culture medium. Cells were spun down and the pellets resuspended in culture medium for plating onto 6-well plates seeded with feeders. One straw was plated per well. Cells were grown for three days before assessing survival.

Colony labeling. Alkaline Phosphatase was detected using a kit (Vector Laboratories, Burlingame, Calif., USA; SK-5200) following the manufacturer's protocol. Antibodies to SSEA-4 (Chemicon International, Temecula, Calif., USA) and Oct-4 (R and D Systems, Minneapolis, Minn., USA) were used at 1:50 following a standard protocol. The cells were visualized through a biotinylated secondary antibody included in the Universal Quick Kit (PK-800) using Nova Red (SK4800) (both from Vector Laboratories, Burlingame, Calif., USA).

Calculation of Survival. Survival was calculated as combined colony number and colony size relative to Group 1, which was set at 100% survival. The horizontal diameters of 10 colonies were measured. These colonies were selected at random by viewing from left to right through the broadest transit through the well (9 o'clock to 3 o'clock) by measuring the first 10 colonies that were growing in isolation, using a micrometer fitted into the microscope eyepiece. All surviving colonies for each treatment were counted.

Karyotype analysis. G-banded karyotype was done through the Cytogenetics Laboratory of the University of Washington.

Results and Discussion

Figure 2:
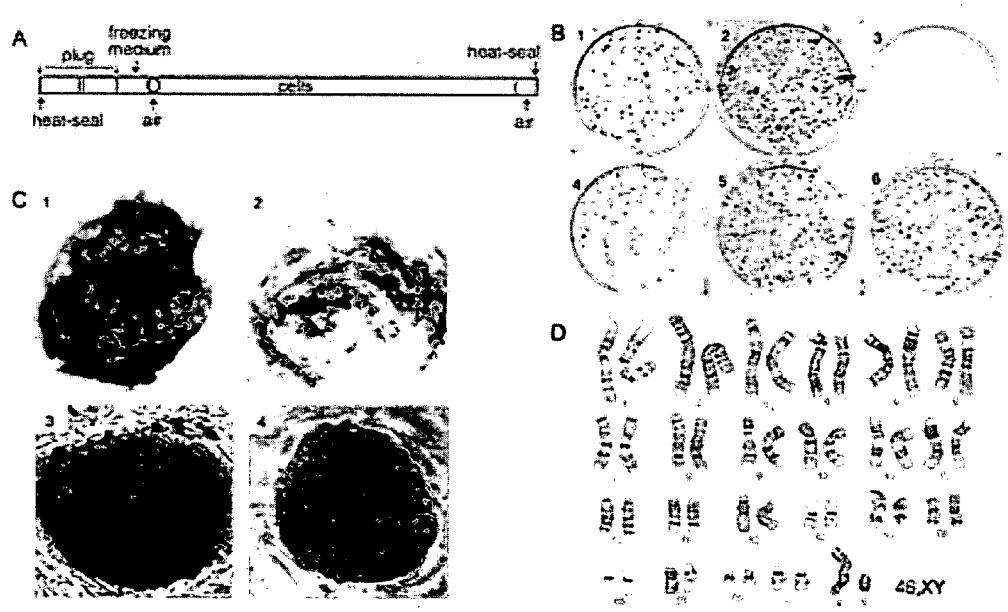
FIGS. 2A-2D. Loading of cells for cryopreservation and analysis of cell colonies post-thaw. A. Schematic of Cassou straw loading pattern. B. Six-well tissue culture plate used for culture of hESC for 3 days following thaw labeled for AP activity (black spots): 1, control (Group 1); 2, cryoprotectant only (Group 2); 3, controlled-rate cooled without seed (Group 4); 4, seed followed by controlled-rate freeze and thaw in room temperature air (Group 5); 5, same as 4, with thaw in room temperature water (Group 6); 6, same as 4, with thaw in 3° C. water (Group 7). C. Labeling of surviving colonies: 1, alkaline phosphatase, predominately undifferentiated colony; 2, alkaline phosphatase, predominantly differentiated colony within the same culture; 3, SSEA-4 immunolabeled colony, undifferentiated; 4, Oct-4 immunolabeled colony, undifferentiated. The size bar represents 100 μm. D. G-banded karyotype of frozen thawed H1 cells.

The Bio-Cool III controlled-rate freezer uses a mechanically refrigerated cold-liquid bath. The Pye freezer (FIG. 1) is a homemade device that contains a liquid nitrogen chamber and an ethanol bath housing a Cassou straw. The two chambers are connected with insulated bundles of copper wires. The rate of controlled cooling is determined by the bundle size and wire gauge; a magnetic stirrer in the ethanol bath ensures homogenous temperature surrounding the straw. To test the suitability of these two devices for freezing hESC, cells were introduced into the Cassou straw by aspiration (FIG. 2A). These straws were then held at room temperature for 20 minutes before being placed at −10° C. and cooled using either a commercial programmable freezer or a homemade Pye freezer. Once thawed, straws were rinsed with ethanol, dried, and the contents emptied directly into culture medium. In all trials, thaw occurred on the day of freeze. Cells were cultured for two to three days and colonies were visualized by staining for alkaline phosphatase activity; sample results for cells tested under six different conditions are shown in FIG. 2B.

All cultures contained some level of spontaneous differentiation that mirrored the control condition. Alkaline phosphatase is a marker of the extent of differentiation: undifferentiated cells express alkaline phosphatase and cells downregulate this factor during initial differentiation (FIG. 2C, panels 1 and 2). In specific cell types, AP expression increases later in differentiation. Therefore, immunohistochemistry against SSEA-4 and Oct-4 was used to confirm the AP observation that the colonies remained undifferentiated on one set of thawed cells (Group 7). Data for immunohistochemistry of SSEA-4 and Oct-4 is shown in FIG. 2C, panels 3 and 4, respectively.

In addition to maintaining cell markers, it is critical that the frozen hESC maintain a normal karyotype upon thaw and reculture. Therefore, G-banded karyotyping was performed on one set of frozen thawed hESC (Group 5); results showing lack of identifiable chromosomal abnormalities or changes to chromosome number are shown in FIG. 2D.

For the purposes of comparing the survival of hESC frozen under different conditions, measures of colony number and size were combined and compared to a control group that was not frozen. Undifferentiated colonies have a flattened morphology with modest cell overgrowth. Neither colony depth nor direct live versus dead cell number were figured into the survival calculation, which compares overall surface area of colonies growing as a monolayer in two dimensions. In addition, slowed growth following cryopreservation would be reflected as reduced survival. Thus, this means of calculating survival may not reflect the absolute survival between groups and could over represent one group relative to another.

Figure 3:
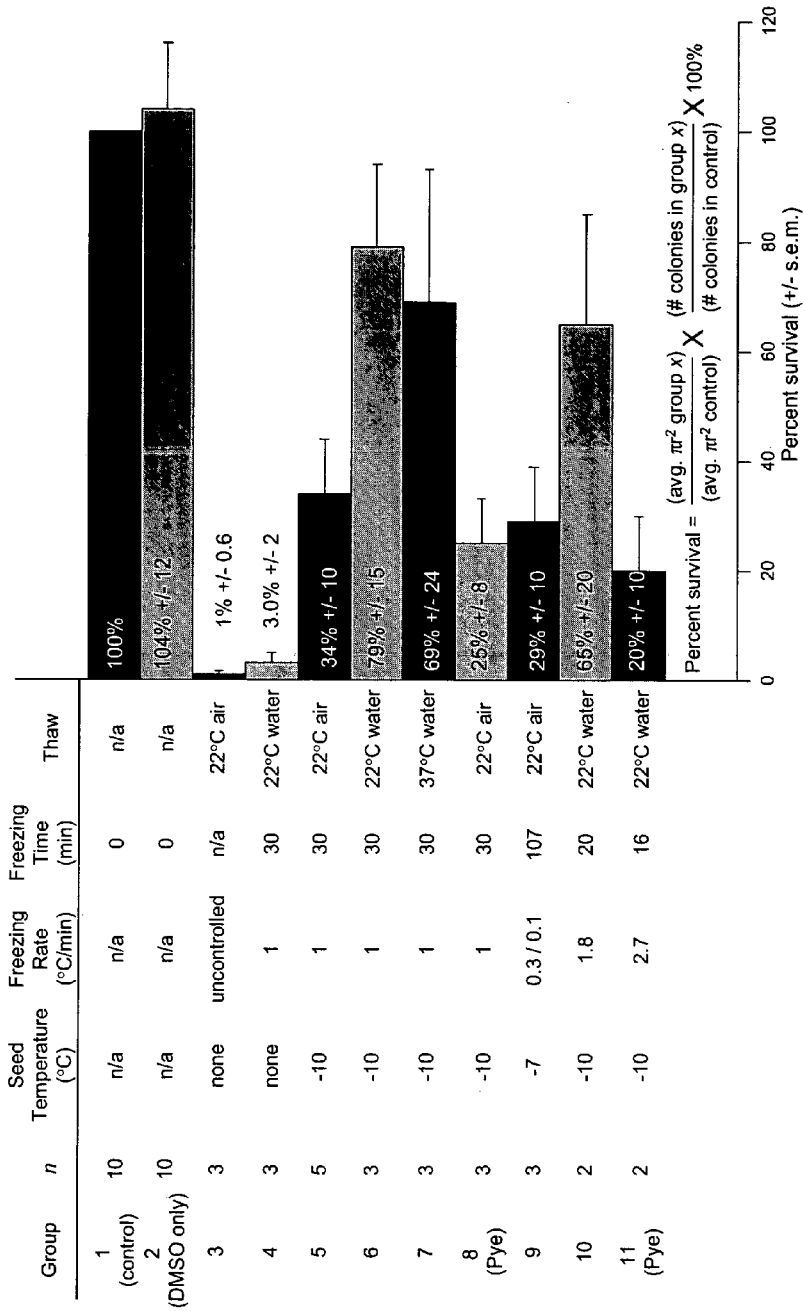
FIG. 3. Combined results of all cryopreservation trials. The groups are represented in table form on the left with the corresponding histogram of survival on the right. Survival was calculated relative to the control (Group 1) using the formula at the bottom of the histogram. For groups 4-8 and 10-11, freezing was performed at the listed rates until a temperature of −33° C. was achieved; cells were subsequently cooled to −196° C. by plunging directly into $LN_2$. For group 3, the cells were placed directly at −80° C., then plunged into $LN_2$ 20 minutes later. For group 9, cells were cooled at a rate of 0.3° C. per minute to −33° C., then cooled at 0.1° C. per minute to reach −35° C., followed by immersion in $LN_2$.

The combined results of all cryopreservation trials, comprising eleven different groups receiving different treatments, are summarized in FIG. 3. There was a relatively high variability in survival between trials within a group. This is in part due to the difficulty in dividing the cells evenly between groups when they are suspended in clusters. However, a number of conclusions can be drawn from the results. DMSO (10%) as cryoprotectant does not appear toxic to the hESC (Group 1 vs. 2, respectively).

Ice crystal seeding, by touching $LN_2$ cooled forceps to the exterior of the straw, is crucial for survival (Group 4 vs. 6 respectively). Survival following room temperature (22° C.) air thaw was poorer than water thaw at either 22° C. or 37° C. (Group 5 vs. 6 and 7 respectively). Thaw was complete in 18 seconds in room temperature water and 105 seconds in air. Survival following use of the inexpensive Pye freezer was equivalent to the BioCool III (Group 8 vs. 5 respectively). However, highest cell survival levels were obtained using the commercial freezer set at a rate of 1-1.8° C./min (Groups 6, 7, and 10). Table 1 describes the freezing protocol to achieve 79% (+/-15%) survival of H1 hESC (Group 6).

We have tested this method using a total of thirteen additional hESC lines (H7, H9, H13, H14, ES1, ES2, ES3, ES4, ES6, BG01, BG02, BG03 and hSF6) and found acceptable levels of cell survival. Some of the lines have been frozen with only a few clusters in the straw and survival was efficient (estimated to be above 50%). In addition, we have frozen the hSF6 cell line in vials instead of Cassou straws and have found survival to be acceptable (estimated ~50% survival) if the liquid volume in the vial is 0.25 ml and the vial is thawed in 37° C. water. Increasing the volume to 1 ml reduced survival to roughly 25%. Thaw rate is slower in vials and is the likely cause for the loss in efficiency relative to straws. Vials represent a greater challenge to seed. We accomplished this by increasing the surface area on one prong of a forceps with a flattened piece of tin foil wrapped around the forcep prong. Effective seed required that the $LN_2$ cooled forceps gently squeeze the vial to achieve contact. The seed travels rapidly in vials relative to straws. The medium appears to be completely crystallized in vials within one minute at -10° C.

The results of this study indicate that slow, controlled-rate cooling as employed for embryo cryopreservation is effective for hESC cryo-storage. The important factors are an ice crystal seed at some point above the temperature of spontaneous intracellular ice formation, in this case -10° C., although trials with -7° C. and -12° C. seed temperatures result in equivalent survival. A freezing rate falling within -0.3 and -1.8° C. per minute is optimal. The plunge temperature of -33° C. is successful, though there is likely leeway that would allow for lower temperatures to be reached prior to $LN_2$ plunge. Thaw should be rapid and can be accomplished using room temperature water in conjunction with 0.25 ml straws. Step-wise cryoprotectant removal upon thaw does not seem to be a requirement. Sucrose was harmful to survival following thaw in our hands. Controlled-rate freezing can be scaled up, making it possible to freeze many straws at one time with little risk of loss of viability. In conclusion, rapid recovery and high viability is achievable by controlled-rate hESC cryopreservation.

The compositions and procedures provided in the description can be effectively modified by those skilled in the art without departing from the spirit of the invention embodied in the claims that follow.

The invention claimed is:

1. A method for the cryopreservation of human embryonic stem cells, the method comprising:
   partially dissociating an in vitro culture of human embryonic stem cells to provide a population of cell aggregates;
   resuspending said cell aggregates in a freezing medium comprising from about 5% to about 15% cyroprotectant;
   placing said resuspended cell aggregates in a closed container for freezing;
   cooling the container to a temperature just below freezing and inducing ice crystal formation of the freezing medium;
   slow cooling said resuspended cell aggregates at a rate not faster than about -2° C./min to a temperature of not higher than about -30° C., followed by a rapid cooling to not higher than about -80° C., to provide a cryopreserved sample;
   wherein upon thawing, the viability of cell aggregates in said cryopreserved sample is at least about 50%.

2. The method according to claim 1, further comprising storing said cryopreserved sample at a temperature of not higher than about -80° C.

3. The method according to claim 2, wherein said storing is in liquid nitrogen.

4. The method according to claim 1, wherein said freezing medium is free of added type IV collagen or laminin.

5. The method according to claim 1, further comprising the step of thawing said cryopreserved sample.

6. The method according to claim 5, wherein said thawing comprising contacting said cryopreserved sample with a bath at a temperature from about 15° C. to 37° C.

7. The method according to claim 1, wherein the ES cell aggregates are prepared by enzymatic digestion of adherent cells to yield aggregates of from about 25 cells, to about 200 cells.

8. A cryopreserved human embryonic stem (ES) cell composition, comprising:
   a suspension of human ES cell aggregates in a freezing medium, prepared by the method according to claim 1, wherein said composition is maintained at a temperature of not higher than about -80° C., wherein upon thawing, the viability of cell aggregates in said cryopreserved sample is at least about 50%.

9. The composition according to claim 8, wherein said freezing medium is free of added type IV collagen or laminin.

10. The composition according to claim 8, wherein the ES cell aggregates are prepared by enzymatic digestion of adherent cells to yield aggregates of from about 25 cells, to about 200 cells.

11. A method for the cryopreservation of primate embryonic stem cells, the method comprising:

partially dissociating an in vitro culture of primate embryonic stem cells to provide a population of cell aggregates;

resuspending said cell aggregates in a freezing medium comprising from about 5% to about 15% cyroprotectant;

placing said resuspended cell aggregates in a closed container for freezing;

cooling the container to a temperature just below freezing and inducing ice crystal formation of the freezing medium;

slow cooling said resuspended cell aggregates at a rate not faster than about −2° C./min to a temperature of not higher than about −30° C., followed by a rapid cooling to not higher than about −80° C., to provide a cryopreserved sample;

wherein upon thawing, the viability of cell aggregates in said cryopreserved sample is at least about 50%.

\* \* \* \* \*

UNITED STATES PATENT AND TRADEMARK OFFICE
CERTIFICATE OF CORRECTION

PATENT NO. : 7,811,819 B2  
APPLICATION NO. : 11/142651  
DATED : October 12, 2010  
INVENTOR(S) : Carol Ware et al.

Page 1 of 1

It is certified that error appears in the above-identified patent and that said Letters Patent is hereby corrected as shown below:

- In column 1, line 3, Immediately following the title please insert
  -- FEDERALLY SPONSORED RESEARCH AND DEVELOPMENT
  This invention was made with Government support under grant no. 1P20GM069983-01 awarded by the National Institutes of Health. The Government has certain rights in this invention. --

Signed and Sealed this
Twenty-sixth Day of July, 2011

David J. Kappos
*Director of the United States Patent and Trademark Office*